United States Patent [19]
Lim

[11] 3,992,516
[45] Nov. 16, 1976

[54] DIRECT FLUORESCENT ANTIBODY COMPOSITION AND METHOD FOR *PNEUMOCYSTIS CARINII*

[76] Inventor: Sook Kyung Lim, 813 Granger Ave., Ann Arbor, Mich. 48104

[22] Filed: Oct. 30, 1974

[21] Appl. No.: 519,217

[52] U.S. Cl. .................................. 424/8; 424/12; 424/85; 424/88
[51] Int. Cl.$^2$ ................. A61K 39/00; G01N 31/22; G01N 33/16
[58] Field of Search ..................... 424/8, 12, 85, 88

[56] References Cited
OTHER PUBLICATIONS

Lim; S., Applied Microbiology, vol. 26, Nov. 1973, pp. 666–671.
Kim; H., PSEBM, vol. 141, Oct. 1972, pp. 304–309.
Goldstein, J. Exptl. Med., vol. 114, 1961, pp. 89–109.
Kwapinski, Method of Immunocheim & Immunol. Res. Wiley–Interscience NY 1972, pp. 18–21, 609–610.

*Primary Examiner*—Albert T. Meyers
*Assistant Examiner*—A. P. Fagelson
*Attorney, Agent, or Firm*—James C. Wray

[57] ABSTRACT

A *Pneumocystis carinii* antiserum conjugated with fluorescein isothiocyanate composition, its use being the detection of *Pneumocystis carinii* organisms and the method of making this composition using an enzyme purifying technique.

20 Claims, No Drawings

DIRECT FLUORESCENT ANTIBODY COMPOSITION AND METHOD FOR *PNEUMOCYSTIS CARINII*

This invention relates to a diagnostic method for the immunofluorescent detection of antibodies for *Pneumocystis carinii* in sputum or tracheal aspirate, and to a method of making this antiserum.

Rejection of transplanted organs has been almost conquered; the major remaining problem which has been causing the deaths of transplant patients has been infections. Moreover, a major cause of infections has been *Pneumocystis carinii*. Major medical research centers have been working on the problems of detecting this disease and curing it for many years.

To date the traditional method of detecting *Pneumocystis carinii* pneumonitis has been dependent upon lung biopsy to obtain tissue samples from a patient's lungs.

I have developed a direct fluorescent antibody (DFA) procedure which has been very accurate in detecting P. carinii in hypopharyngeal smears, sputum or tracheal aspirates from rats whose infection had been activated by corticosteroid administration and from humans who are known to have the disease.

The need for a rapid and reliable laboratory diagnostic procedure has been emphasized because of the increased frequency of P. carinii pneumonitis associated with the wide use of immunosuppressive chemotherapy. This therapy is widely used in treating cancer and in transplant operations.

Currently, the diagnosis of P. carinii pneumonitis mostly depends on biopsy of lung with examination of the tissue by the conventional silver impregnation technique Bradshow, et al, "Pneumocystis Carinii Pneumonitis: Diagnosis and Treatment". Ann Intern Med. 73:775-777 (1970), Robbins, "Pneumocystis Carinii Pneumonitis: A review". Pediat. Res. 1:131-158 (1967). A reliable method using sputa or tracheal aspirates would be simpler and safer; however, with current staining procedures the examination of such specimens has been less often successful than biopsy in the detection of P. carinii Cohen, et al, "*Pneumocystis carinii* pneumonia; Percutaneous lung biopsy and review of literature." Chest 60:195-199 (1971); B. Jacobs, et al, "Needle biopsy in *Pneumocystis carinii* pneumonia". Radiol. 93:525-530 (1969); D. Johnson, et al, "*Pneumocystis carinii* pneumonia in children with cancer: Diagnosis and treatment". JAMA. 214:1067-1073 (1970); L. Rosen, et al, "*Pneumocystis carinii* pneumonia: A clinicopathologic study of twenty patients with neoplastic diseases". Amer. J. Med. 53:428-436 (1972); J. Ruskin, et al, "The compromised host and infection. I. *Pneumocystis carinii* pneumonia". JAMA 202:1070-1074 (1967). The value of conventional staining methods for tracheal aspirates or sputa is controversial. The need for controls of the procedure at all points is emphasized. Although there is great need for a reliable diagnostic method for P. carinii infection, there is no report on the use of fluorescent antibody method as a diagnostic procedure for detecting it.

This invention relates to an anti-pneumocystis antibody that is conjugated with a fluorescent dye which is an antiserum against *Pneumocystis carinii* organisms. An important part of this process resides in the use of enzymes which I have found purify the antigens. I have found that trypsin is the most effective purifying enzyme. Trypsin is a proteolytic enzyme and it cleaves all peptide linkages in the substrate proteins whose carbonyl groups are provided by arginine and lysine specifically. It is maximally active at pH 7.0 and fast reaction can be achieved at 37° C. The concentration range is between 0.05% – 0.3. It has become a common practice to use trypsin in tissue culture laboratories in dispersing tissues.

There are other protolytic enzymes that may be used in place of trypsin namely, chymotrypsin, pepsin, collagenase, pronase, etc. but no other enzyme is as specific as trypsin in their chemical reaction.

The purpose of using the enzyme here is to digest out serum proteins in the tissue homogenate, including the proteins that had been bound to the parasitic cell walls. Thus this process will leave the organisms relatively free from such contaminants.

Further purification of the antigen was carried out by the use of sucrose gradients In this process organisms of identical density were collected on the corresponding sucrose layers, then the individual fraction was washed separately. After examining organisms of each gradient for their morphology, purity, and antigenicity by fluorescent antibody and May Grunwald giemsa staining method, the antigen was used in the immunization of rabbits for hyperimmune serum and also as an excellent substrate antigen for the indirect fluorescent antibody (IFA) tests and as positive control antigens.

For the immunization of rabbits (p. 667) the organism was sonicated with a Ratheon sonic oscillator. By this process most of the organisms were disrupted, although some of them remained only partially damaged. Since the exact composition of antigen or antigenicity is not known, the whole material (i.e. cytoplasmic portion of proteins and organells, RNSs, cell walls and nuclear materials so force) was used in the immunization.

Because of inability to cultivate P. carinii organisms in vitro it is very difficult to obtain the antigen or the organism in the pure form. The organism multiplies primarily in the lung tissue, in the alveolar spaces specifically, under certain circumstances, such as in immunological deficiency states. The organisms are firmly aggregated to each other, mixing with inflammatory products of the host within alveolar spaces. Therefore, in order to obtain the organisms from the tissue, the lung tissue had to be minced with mortar & pestle with sand or waring blender.

And more specifically, to prepare P. carinii antigens P. carinii organisms were obtained from minced lung tissue of 200-g naturally infected rats of either sex, injected with cortisone acetate (Merck, Sharp and Dohme) (25mg) subcutaneously twice weekly for 8 weeks or until fatal pneumocystosis developed. This was done using the technique described in Frenkel et al (1966), Lab. Invest. 15:1559-1577. Chlortetracycline (0.05%) and amphotericin B (0.05%) were given in the drinking water throughout the experimental period to prevent secondary infection during corticosteroid treatment. P. carinii organisms of human source were taken from lung tissue obtained at necropsy from histologically proven PP patients-four from the Center for Disease Control, Atlanta, Georgia, and one from St. Jude Children's Hospital, Memphis, Tennessee. All specimens were re-examined for degree of infection by May-Grunwald-Giemsa (MGG) staining.

The infected lung tissue was homogenized, using mortar and pestle, in Eagle minimal essential medium with Hank solution (MEM) containing 100 U of penicillin per ml and I mg of streptomycin per ml, and clarified by low-speed centrifugation at 400 rpm for 3 min, discarding the sediment. To the supernatant fluid a sample of warmed 0.25% trypsin (General Biochemicals, Chagrin Falls, Ohio) was added, and the mixture was incubated at 37° C for 10 min. and centrifuged at 900 rpm for 10 min. After the sediment had been discarded, the supernatant fluid was recentrifuged at 3000 rpm for 30 min. This final sediment was reconstituted to make a 10 or 20% suspension of organisms by volume in MEM. The suspension was fractionated by sucrose density gradient centrifugation in cellulose nitrate tubes with the following sucrose concentrations: 12, 24, 36, 48, and 60%, respectively. A 20-ml fraction of a 5% *P. carinii* sample were placed on top of the gradient and centrifuged at 2500 rpm for 60 min. at 4° C. A 21-gauge hypodermic needle was used to puncture the bottom of the tube, and drops of the visible zones were collected in separate tubes. The fractions were washed and centrifuged as above. These organisms were quantitated and used in the immunization of the rabbits and as slide preparations for DFA or IFA staining. In calculating the number of organisms, the standard method for the examination of dairy products was followed which was described in Thompson et al (1972), Direct microscopic method, p. 158–175. In W. J. Houser, Jr. (ed), Standard methods for the examination of dairy products, 13th ed. American Public Health Association, Washington, D.C.

To produce purified antibodies, first of all, it is necessary to isolate the globulin fraction containing specific antibody molecules against *P. carinii* antigens, from hyperimmune serum of rabbits.

The antisera obtained by using either rat *P. carinii* or human *P. carinii* organisms were fractionated with saturated ammonium $(NH_4)_2 SO_4$ solution (pH 7.0) by the Marshall et al, 1959 procedure described below. After mixing an equal volume of antiserum and saturated ammonium sulfate solution, it is incubated overnight at 4° C. Then by subsequent centrifugation the globulin fraction is precipitated and albumins, and euglobulins remain in the supernatant fluid and are discarded.

In the preferred embodiment described below, rabbits were used. However, other animals such as horses, dogs, etc. could also be used.

Since the reliability of the fluorescent antibody technique depends primarily on the specific reaction of the antiserum used, a careful examination of the antibodies was carried out to test their specificity.

In order to increase the specificity, it was necessry to remove non-specific antibody components that might have been acquired during multiple injections. This was done to remove antibodies directed against common antigens and with rat's serum to eliminate antibodies produced against rat serum protein components.

More specifically to prepare the antiserum rabbits weighing 1.5 to 2.5 kg were used. A primary series of immunizations consisted of four consecutive injections once a week; 0.1 ml of $6 \times 10^6$/ml, or approximately 600,000 organisms, was thoroughly mixed with complete Freund adjuvant and injected into the footpads. In some cases the organisms were sonically disrupted in a 10-kc Raytheon sonic oscillator, run at 60% maximal output for 10 min.; in others, whole organisms were injected. After an interval of 6 weeks, a series of four booster injections were given intravenously at 3 to 4 day intervals twice a week, gradually increasing the number of organisms $10^5$, $2 \times 10^5$, $5 \times 10^5$, and finally $10^6$.

Serum samples on the day after the last injection were titrated for antibody by immunodiffusion and IFA tests in comparison with preimmunization sera. All tests were made both before and after absorption of the antiserum with mouse powder or normal rat serum. Ouchterlony immunodiffusion (ID) plates were prepared using 1% Noble agar method in Barbitone buffer (pH 8.0) with Merthiolate in a 1:1000 final concentration. Serum samples in serial dilutions were placed in outer wells, and either sonically treated antigens or extracted antigens were placed in the center wall. The plates were incubated at room temperature and read at 24, 48, and 72 h. The absorbed antisera were also titrated by IFA and labeled goat antirabbit immunoglobulin (Ig) G. Precipitin bands were observed: The hyperimmune sera before absorption showed several precipitin bands on Ouchterlony ID plates but the serum after absorption with mouse powder and/or normal rat serum or human serum for antiserum for *P. carinii* of human sources there remained a single precipitin band which was considered to be the *P. carinii* specific reaction.

The absorption procedure consisted of adding 100 mg per ml of dry mouse powder to the antiserum mixed thoroughly and centrifuged at 12,000 rpm for 30 minutes after standing one hour at room temperature. Although the tissue powder used for absorption is usually from the tissue to be examined or from another organ of an animal of the same species, mouse powder is frequently used for efficient and universal absorption of nonspecific fluorescence.

Fluorescent Isothyocyanate (FITC) has the following chemical formula: $C_{21}H_{11}O_5NS$ and is the best dye available for the fluorescent antibody (FA) technique in terms of fluoresce efficiency, stability, and combining capacity with proteins. The dye has greenish-yellow fluorescence and a molecular weight of 389.4; maximum wave length of absorption = 490mM and maximum wavelength of emission = 520mM.

When the FITC dye is reacted with an alkaline solution of antibody protein, a thiocarbamide bond is formed with the free amino groups (mainly the e-amino group of lysine residue) of the protein, forming labeled antibody as follows:

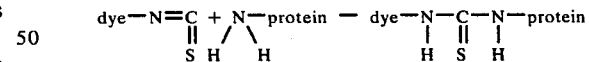

The desirable molar ratio of FITC to protein (compounds with a molar combining ratio = F/P) is 1 to 3. This ratio is important because increasing the ratio (i.e. over 4) increased the nonspecificity.

Other known fluorescent dyes can be substituted for this dye, such as fluorescein isocyanate (FIC) which is seldom used at present because of its extreme lability of denaturation of the antibody or reduction of its activity, dyes of the rhodamine series such as tetramethyl rhodamine and tetraethyl rhodamine compounds are the isocyanate preparations, etc. The rhodamine dyes are not as stable as FITC and only weakly fluorescent but are the safest of the red-brown powders and have an orange-red fluorescence. The dyes cannot combine with protein by themselves, they must be used for labeling after prior treatment with phosphorus Pentochloride (PCl$_5$). Labeling of the purified specific antiserum with tetraethyl rhodamine may be used in the identification of P. carinii in the tissue sections (of necropsy or biopsy material).

To conjugate the antiserum with FITC we added 10 ml of antiserum to an equal volume of saturated ammonium sulfate solution (pH 7.0) and the mixture was incubated in the cold (4° C) overnight.

The material was then centrifuged at 9,000 rpm at 4° C, after which the supernatant fluid was discarded and the precipitate was dissolved in 5 ml of 0.85 % NaCl as described in Marshall et al (1958), Marshall, J. D., W. C. Eveland, and C. W. Smith, "Superiority of fluorescein isothiocyanate (Riggs) for fluorescent antibody technique with a modification of its application." Proc. Soc. Biol. Med. 98:898–900.

This solution, containing the globulin fraction, was dialyzed against pH 7.6 buffered saline (PBS) overnight to eliminate ammonium ions. Protein content of the globulin solution was determined by the biuret method with a Beckman spectrophotometer at a wave length of 540 nm. The sample was diluted with 0.85% NaCl and carbonate-bicarbonate buffer (pH 9.0) so that the final solution contained 10 mg of protein per ml and 10% carbonate-bicarbonate buffer, and then cooled to 4° C. To this was added 0.025 mg of fluorescein isothiocyanate (FITC) per mg of protein, and the mixture was stirred overnight at 4° C. The conjugate was transferred to a cellulose membrane and dialyzed against pH 6.3 0.175 M phosphate buffer (PB) overnight, with one change of the buffer solution. The conjugate, freed from unbound dye, was fractionated in a diethylamino-ethyl-cellulose anion exchange column (1.5 by 30 cm) to obtain the fraction of optimum F/P ratio of antibodies. The DEAE cellulose ion exchange is one of the most efficient methods of separating and purifying proteins.

These fractions were equilibrated with PB, pH 6.3 using the method described in J. Riggs et al, 1958. "A simple fractionation method for preparation of fluorescein-labeled gamma globulin." Proc. Soc. Exp. Biol. Med. 105:655–658. Using Riggs process to separate the labeled antibody molecules, elution was made with 0.125 M salt, such as sodium phosphate in PB (pH 6.3), and the stepwise fractions were collected, put into dialyzing bags separately, and dialyzed against pH 7.6 PBS overnight at 4° C. The molar fluorescein protein ratio was determined from the respective values of optical density at 376 nm (OD$_{376}$) and OD$_{493}$ on each fraction and of the purified antiserum, using the nomogram for molar fluorescein/protein ratio in Wells et al, "Rapid fluoresceing and protein assay method for fluorescent antibody conjugates". Appl. Microbiol. 14:271–275.

The DFA staining procedure consisted of taking smears from purified P. carinii or trypsinized impression smears of infected tissue which were fixed with acetone at room temperature for 10 min. Tissue smears were incubated with 0.25% trypsin at 37° C for 10 min and washed in PBS (pH 7.6). The working dilution of the labeled antiserum, previously evaluated, was placed on the fixed smears on the slides, incubated at room temperature for 45 min, and washed twice with pH 7.6 PBS for 10 min each. The slides were then counterstained with a 1:20 dilution of Eriochrome Black for 5 s and mounted in buffered glycerin. This technique is described by Hall, et al, 1962. "Chelated azo dyes used as counterstaining in the FA technique." Zentrabl. Bakteriol. Parasitenk. 184:548–554.

Eriochrome Black is a chelating substance used to counterstain fluorescent preparations. It has an absorption peak of about 520mM at a pH of 3.0 which coincides with the maximum emission peak of FITC. It removes nonspecific staining by removing the ionic bridges formed between overcoupling of antibody and tissue other than the specific antigen.

For evaluation of sensitivity in identification of the various forms of the organisms, the DFA test was compared with conventional staining. Two sets of smears were made from infected lung tissue of the same animal; one set was stained by DFA and the other with MGG. Using a fixed counting time for both methods, the number of parasites counted within that time limit was used to determine whether the DFA procedure was superior in terms of rapidity of identification of the parasites.

Hypopharyngeal (H-P) material was taken from the rats twice a week, two swabs being taken each time, using sterile nasopharyngeal swabs (Calgiswab, Colab) under light ether anesthesia. The swabs were either treated in N-acetyl-L-cysteine (NALC) solution or directly smeared on microscope slides. To homogenize the mucous H-P material, the swab specimens to be treated were immersed in 1 ml of 2.5% NALC (pH 8.0) in siliconized tubes for 15 to 30 min, followed by centrifugation at 2,500 rpm for 20 min. The supernatant fluid was discarded, the sediment was washed with Hanks balanced salt solution, and microscope smears were prepared from the sediment.

Each smear was made with 0.01 ml of NALC-treated specimen or with the material from one direct swab. The enumeration of parasites was performed by counting all organisms in a smear.

The number of stained cysts in each smear was expressed by a score. Because a smaller number appeared in H-P material than in lung tissue the scores are necessarily different (Tables 1 and 2).

TABLE 1

| SCORE | Testing the DFA procedure in H-P material from rats | |
|---|---|---|
| | H-P material (cysts/smear) | Lung Tissue (cysts/smear) |
| — | 0 | 0 |
| ± | 1 | 10 |
| 1 | 2–4 | 10–100 |
| 2 | 5–9 | 100–500 |
| 3 | 10–14 | 500–1,000 |
| 4 | 15 or more cysts with aggregates | 1,000 |

TABLE 2

Pneumocystis score in hypopharyngeal smears and lung tissue of rats by direct fluorescent antibody technique

| RAT NO. | HYPOPHARYNGEAL SMEAR[a] | LUNG TISSUE[b] |
|---|---|---|
| 28 | 3 | 2 |
| 31 | 4 | 3 |
| 32 | 4 | 2 |
| 33 | 1 | 1 |
| 37 | 3 | 2 |
| 42 | 3 | 1 |
| 51[c] | 2 | 3 |
| 54[c] | 4 | 4 |

TABLE 2-continued

Pneumocystis score in hypopharyngeal smears and lung tissue of rats by direct fluorescent antibody technique

| RAT NO. | HYPOPHARYNGEAL SMEAR[a] | LUNG TISSUE[b] |
|---------|-------------------------|----------------|
| 55[c]   | 2                       | 2              |

[a]Hypopharyngeal smears taken at death or during week preceding death.
[b]Lung tissue impression smears made at death.
[c]Died after corticosteroid was withheld.

To express the relative number of cysts in the lung tissue stained by DFA, an impression smear measuring approximately 1 cm$^2$ was prepared, and the entire smear was examined under high, dry power. Tissue samples were taken from the most consolidated area under gross examination, with at least 10 smears being made from each specimen.

H-P materials of untreated animals in the control group were also taken once a week in the same manner as the treated animals, from the first day of the experiment through 5 weeks. After the animals were sacrificed, re-examination was made by DFA of impression smears of lung tissue as well as tissue of the ascending respiratory tract for presence of *P. carinii* organisms. The intact bronchi and trachea were dissected by sterile technique and saline-lavage was made with a 2-ml syringe fitted with a 23-gauge needle. The material was centrifuged, and smears were prepared in the same manner as for the H-P material.

The fractions of *P. carinii* organisms obtained by centrifugation of the sucrose gradients at 2,500 rpm for 60 min at 4° C were as follows. Organisms believed to be trophozoites of small size, obtained at 36% aqueous sucrose solution, specific gravity (SG) 1,1562; large trophozoites and some cyst forms, obtained at 48% aqueous sucrose solution, SG 1,2186; and some precystic forms and cysts in the sediment fraction, 60% aqueous solution, SG 1,2865. The fractions obtained at 48 and 60% sucrose were combined, centrifuged, and washed, and the organisms were suspended in physiological saline to make a 20% concentration (approximately 7.5 × 10$^6$ to 10 /ml, standard method of direct microscope counting).

The rabbit hyperimmune sera prepared against *P. carinii* organisms of rat origin reacted with the sonically disrupted soluble portion of antigen to give several precipitin lines on Ouchterlong ID plates. After absorption of the serum with mouse powder and normal rat serum, there remained a single precipitin line which was considered to be the *P. carinii* specific reaction. The titers of antisera from three rabbits (numbers 2, 4, and 5) before conjugation were 1:160, 1:320, and 1:128, respectively, by IFA. Hyperimmune sera prepared with *P. carinii* organisms of human origin exhibited multiple precipitin lines in reaction to sonically treated *P. carinii* organisms from human sources. This antigen reacted with antihuman IgG on ID, suggesting that the human *P. carinii* had surface-bound globulins. After absorption of the immune serum with normal human serum, a single precipitin line remained. This line was eliminated with a sample of antiserum which was incubated with human *P. carinii* antigen overnight at 4° C.

The pooled fractions of labeled antibody were used for determination of molar fluorescein/protein ratio and protein concentrations. The mole F/P ratios ranging from 1.0 to 5.0 and protein concentrations from 1 to 5 mg/ml were chosen for titration.

The purified *P. carinii* from rats, stained with approximately diluted labeled antiserum, exhibited brilliantly delineated organisms of various sizes and shapes. The cystic wall stained intensely in all organisms, but cytoplasmic staining varied somewhat from one organism to another. Some apparently immature organisms showed strong staining of both internal structures and the external membrane. In the large cysts that were considered to be mature forms or degenerating organisms, the FA staining was found mainly in the external membrane, whereas the internal portion of the cysts showed mostly the counterstaining. With the labeled anti-rat *P. carinii* antiserum, *P. carinii* from both rat and human sources showed brilliant staining. The staining characteristics of various forms of human *P. carinii* did not differ noticeably from those of rats. The labeled antihuman *P. carinii* antibody reacted with *P. carinii* from rats as strongly as with human *P. carinii*. With this antiserum, the *P. carinii* in the tissue smears of both rats and humans showed the characteristic, intense membrane staining with less brilliance of the internal cystic portion of the parasites. With trypsin-treated tissue preparations, the intensity of the staining was enhanced, so that aggregated masses of parasites and single organisms on the slide were clearly delineated. In IFA tests *P. carinii* from man and rats showed the same cross-reactions seen in the DFA procedure.

The following control procedures demonstrated the specificity of the reaction. (i) Labeled normal serum, whether from rabbits or man, did not stain either animal or human *P. carinii*, (ii) After absorption of the labeled antibody with concentrated *P. carinii* the fluorescence was eliminated. (iii) In the two-step staining, the fluorescence was markedly reduced by unconjugated antiserum. (iv) Uninfected tissue from animal and human lungs showed no fluorescence. (v) Staining of other species of microorganisms obtained from appropriate cultures with labeled anti-*P. carinii* antibody showed no cross-reactions. Organisms tested were: *Candida albicans, C. tropicalis, Blastomyces dermatiditis, Cryptococcus neoformans, Rhodutorula sp., Histoplasma capsulatum*, and microorganisms usually present in the respiratory tract, such as group *A streptococci*, *Staphylococcus, Diplococcus pneumoniae, Haemophilus influenzae, Escherichia coli*, and *Pseudomonas sp.*

Various forms of *P. carinii* were detected in H-P materials of rats treated with cortiocosteroids. *P. carinii* were detected in rats as early as 2 weeks after corticosteroid treatment was started. Nine animals were positive by 5 weeks, 14 by 7 weeks, all 16 by 9 weeks. The average number of organisms detected in the H-P smears increased with time, reaching a peak at 9 weeks. *P. carinii* were demonstrated in the H-P material for a prolonged period after the corticosteroid treatment had been terminated. The *P. carinii* score in the H-P remained at the peak for 2 to 3 weeks, thereafter declining to lower levels until 8 to 9 weeks. Of 3 animals that survived beyond 9 weeks, 2 were negative from the 10th week continuously until the 13th week, whereas one showed intermittent excretion of organisms up to the 13th week. The numbers of *P. carinii* in the lung tissue were relatively well correleated with the numbers in H-P smears.

*P. carinii* were demonstrated in the H-P material of convalescent animals after discontinuation of corticosteroids. They were detected in one animal as long as 8 weeks, in the upper respiratory tract as well as lung tissue. In another animal, which died 6 weeks after the discontinuation of cortisone acetate, there were many cystic forms that were in regression, but the parasites were not detected in the upper respiratory tract.

The untreated animals showed rare organisms in H-P material. Occasional organisms (±) were detected in 2 of 10 rats on 5 weekly examinations. Rare organisms were found at autopsy in these two rats and two additional animals.

For evaluation of rapidity and accuracy in identification of the various forms of the organisms the DFA was compared with MGG staining. In infected lung tissue of different animals, the numbers of organisms counted in 10 min were 8 to 16 times (mean 11 times) higher with the DFA method that with MGG staining. Free forms and trophozoites were found predominantly during the acute stage of PP, whereas most of the organisms detected by DFA during the convalescent period were cysts. MGG staining demonstrated pre-cystic forms and mature cysts; however, the free forms and small trophozoites were difficult to differentiate from the cellular background by this method, as shown in Table 3.

the antigen, thereby insuring greater specificity of the tests.

IFA studies show that anti-rat *P. carinii* antiserum reacted only with *P. carinii* from rat but not with organisms from humans. However, their results cannot be compared with the results in the present study, since different procedures were used for the preparation of antigens. For example, the organisms they used for injection of animals and for IFA tests were not isolated by enzyme treatment of the tissue as in this study.

In this study no organisms other than *P. carinii* were stained with the conjugated anti-*P. carinii* sera used. However, each antiserum should be tested against other microorganisms which might be mistaken for *P. carinii* in the DFA test. The need is illustrated by the finding of Kendrick et al., 1961, "Fluorescent antibody techniques. Methods for identification of Bordetella pertussis." Amer. J. Dis. Child. 101:149–154, that one conjugated antipertussis serum stained both Bordetella pertussis and staphylococci; the conjugated preinjection sample also stained staphylococci but not *B. pertussis*.

Sensitivity of the DFA procedure has been demon-

TABLE 3.

Comparison of direct fluorescent antibody technique and May-Grunwald-Giemsa staining for detection of *P. carinii* in lung tissue (number of parasites in 10 min.)

| RAT NO. | FREE FORMS | | TROPHOZOITES | | MATURE CYSTS | | TOTAL | |
|---|---|---|---|---|---|---|---|---|
| | DFA | MGG | DFA | MGG | DFA | MGG | DFA | MGG |
| 27 | 234 | 1 | 120 | 16 | 108 | 11 | 462 | 28 |
| 31 | 211 | 5 | 169 | 20 | 169 | 28 | 490 | 53 |
| 51 | 100 | 6 | 108 | 15 | 90 | 16 | 290 | 37 |
| 54 | 190 | 8 | 131 | 22 | 169 | 10 | 490 | 59 |
| 55 | 39 | 0 | 54 | 5 | 88 | 29 | 181 | 15 |

The specificity of a diagnostic antiserum depends on the purity of the antigen used in its production and staining may be inhibited by a blocking phenomenon. A coating of the antigen with antibody or other substance may compete with the specific *P. carinii* antibody. In the antisera used in this study, special attention was given to purification of the antigens for immunization of the rabbits. It appears that little, if any, of the reactivity observed is directed to rat lung antigens, since antisera were absorbed with both normal rat serum and mouse powder, antigens from human sources gave strong reactions, and only one line of identity was seen in ID tests. As indicated by the results with trypsin-treated tissue preparations, it was possible to remove the blocking antibody which could be demonstrated as a coating of the *P. carinii* organisms in untreated preparations. The results indicated a high degree of specificity of this method.

Although antigenic relationships between *P. carinii* from human and animal sources were demonstrated by the results of DFA and IFA cross-reaction tests, there was a difference in antibody titers between homologous and heterologous systems. The higher titer in the homologous system observed in all tests suggested that *P. carinii* from different species may not be entirely identical, although they may share the greater part of their antigenic specificity. The use of organisms grown in a different host may be of advantage in the identification of *P. carinii* by the DFA procedure or when *P. carinii* are used as IFA antigens, since the heterologous reagent reduces nonspecific staining of host material in strated by comparing it with MGG, a conventional staining method, in terms of timesaving and accuracy. Whereas MGG identified only mature cysts by staining the intracystic bodies, the DFA method demonstrated all forms of the developing organims.

The DFA procedure, described above provided greater sensitivity than conventional staining techniques in the examination of hypopharyngeal smears of rats. In further clinical studies the reliability of the procedure was tested on specimens of sputum and tracheal aspirate of human origin and similar sensitivity results were obtained.

The chief sources of clinical specimens were The University of Michigan Medical Center in Ann Arbor and Children's Memorial Hospital in Chicago. The specimens were obtained from patients in respiratory distress who developed varying degrees of pulmonary infiltration as demonstrated radiologically. Most of these patients had immunological deficiency diseases of various types or were receiving immunosuppressive chemotherapy or adrenocorticosteroids for cancer.

A total of 108 specimens of sputum or tracheal aspirate were studied from 68 patients with clinical indications of *P. carinii* pneumonitis (PP). Thirty-five of the patients had strong evidence of PP; in 33 others the clinical findings merely suggested *P. carinii* infection. Ten patients were known to have congenital immunological disorders with histories of recurrent infection of the respiratory system; 48 patients were receiving immunosuppressive therapy for lymphoreticular neoplasms or other types of malignancy; and the remaining 10 patients were in other categories.

Control studies were carried out on 70 sputa or tracheal aspirates from 50 patients who had acute infectious disease of the lower respiratory tract but no clinical basis for suspicion of PP. These specimens were collected primarily for bacteriological culture.

Single specimens were obtained from most patients, but in some cases additional specimens were examined. When a patient was found to have a positive DFA test for *P. carinii*, paired sera, when available, were tested by the indirect fluorescent antibody (IFA) method for rises in antibody titers. Histologic corroboration was sought whenever possible. The histological examinations included the methenamine silver staining technique.

Because of their viscosity, most of the specimens were treated by a mucolytic process. The specimens were tested both before and after treatment. For homogenization of tracheal aspirates or sputa, a freshly prepared N-acetyl-L-cysteine(NALC) solution was added to the specimen in the original container to make a final concentration of 0.25 to 0.3% NALC. The material was mixed thoroughly until visible mucolysis occurred, then it was incubated at room temperature for 10 to 20 min. For the purpose of concentration, 1/N NaOH-trisodium acetate mixture was added to make a final concentration of 1% using the procedure described by Dye and Kubica for *Mycobacterium tuberculosis*, "Tuberculosis and other mycobacterioses", pp. 160–162, 5th ed. In: Bodily, H.L., E. L. Updyke, and J. O. Mason, (eds), Diagnostic Procedures for Bacteria, Mycotic and Parasitic Infections. 5th ed. 1970, pp. 160–162. After thorough mixing, the specimen was transferred to a siliconized centrifuge tube with at least 4 volumes of 0.85% saline solution. The mixture was then either allowed to stand at room temperature for 10 to 20 minutes or centrifuged at 400 rpm for 1 minute to eliminate coarse particles. The supernatant fluid was transferred to another tube and was centrifuged at 3000 rpm for 20 to 30 minutes. The sediment was used as a concentrated specimen. Hypopharyngeal swabs were directly smeared on microscope slides or treated in the NALC (pH 8.0) for 15 to 20 minutes, followed by centrifugation at 2500 rpm for 20 min. Smears for microscopy were prepared from the saline-washed sediment.

Smears were made routinely with the unprocessed sputa or tracheal aspirates. Portions of raw specimens were spread thinly with a 3 mm bacteriological loop on clean microscope slides. The homogenized as well as the concentrated specimens were spread in the same way. All smears were air dried at room temperature. Usually the smears from the raw and homogenized specimens were stained while the concentrated smears were being processed. If *P. Carinii* was identified in sufficient number from raw and homogenized smears, the concentration process was omitted.

Using the same method described above, the DFA reagents were prepared. In brief, the staining procedures were as follows: The labeled anti-*P. carinii* antibody, prepared from either human or animal sources, was placed on the smear and incubated at room temperature for 45 min., followed by 2 washings with pH 7.6 phosphate buffered saline (PBS) for 10 minutes each. The slides then were counterstained with a 1:20 dilution of Eriochrome Black for 5 seconds, using a method described by C. Hall, et al, "Chelated azo dyes used as counterstaines in the fluorescent antibody technic". Zentr Bakt Parasit. 184:548–554 (1962), and were mounted in buffered glycerin. In most instances 6 to 8 smears were examined, and the mean number of *P. carinii* per smear was recorded. Control specimens were handled in the same way as the test specimens, including the concentration steps.

Serum antibody titration was accomplished by using the following Indirect Fluorescent Antibody (IFA) technique. The smears of *P. carinii* from rats were first incubated with serial two-fold dilutions of the test sera, followed by 2 washings in phosphate buffered saline PBS, pH 7.6 for 10 minutes each. The smears were then covered with either dilution for another 45 min. at room temperature. The smears were counterstained and mounted as usual.

The methenamine silver nitrate staining procedure was carried out as described above by the method of Gomori as described by Grocott in R, Grocott, "A stain for fungi in tissue sections and smears using Gomori's methenamine-silver nitrate technic." Amer. J. Clin. Path,25:975–979 (1955).

*P. carinii* antigens and specific antiserum for DFA staining were prepared using the method described above. In brief, rabbits were injected with relatively purified *P. carinii* organisms from either human or animal sources. Hyperimmune serum thus obtained was conjugated with fluoresceine isothiocyanate, after proper absorption and evaluation of its specificity.

Preliminary tests show that *P. carinii* from both man and animals were not damaged by the mucolytic process employed in these examples. After at least 30 minutes in 1/N NaOH (pH 14) the parasites showed intense staining with specific labeled antiserum; after 60 minutes some organisms had begun to disintegrate, showing odd shapes. Treating the organisms for 60 minutes with the reducing agent, 3% NALC (pH 8.0) alone, did not change either the morphologic appearance or the surface antigen.

The viscosity of sputa or tracheal aspirates varied from one specimen to another. The mucolytic activity of a 0.3% final concentration of NALC solution at pH 8.0 was efficient in homogenizing the specimen within 1 to 5 min. For the tracheal material this homogenization process alone, without further concentration was sufficient for the detection of *P. carinii*. However, the concentration step was necessary for specimens which showed few or no organisms in unconcentrated material. Nasopharyngeal swabs, treated in 2.5% NALC solution, were also suitable for detecting *P. carinii* after one washing with saline; the sediment obtained by centrifugation contained well-preserved cellular background and parasites.

*P. carinii* from clinical specimens were identified by Direct Fluorescent Antibody Method DFA. A total of 108 specimens from 68 patients with diffuse interstitial pneumonitis were examined by DFA technique. *P. carinii* were identified in 33 patients. Clinical and radiologic evidence for PP was strong in 25 of these, and suggestive in 8 as shown in Table 1. The 50 patients with negative evidence and not suspected of having PP were considered as controls. The results with 70 specimens from the 50 control patients are included in Table 4. *P. carinii* were detected in 3 of these individuals on one or more examinations.

TABLE 4

Correlation between Direct Fluorescent
Antibody Tests of Specimens and Clinical
and X-ray findings of the Patients

| clinical and X-ray Criteria of P. carinii Pneumonitis | No. of Patients with Direct Fluorescent Antibody Test | | |
|---|---|---|---|
| | Positive | Negative | Total |
| Strong positive | 25₁₃₃ | 10₁₃₅ | 35₁₆₈ |
| Suggestive | 8 | 25 | 33 |
| Negative (Controls) | 3 | 47 | 50 |
| Total Patients | 36 | 82 | 118 |
| Agreement | 33/36=91.6% | | 47/82=57.3% |

In Table 5 the results of histologic examination (methenamine silver) on the 15 patients from whom tissues were obtained by biopsy or necropsy are recorded. Of 11 patients positive by DFA, 9 were also positive histologically. Of the four negative by DFA, all were negative by histologic findings.

TABLE 5

Correlation between Direct Fluorescent
Antibody Test of Sputa or Tracheal
aspirates and Subsequent Histological
Examination for P. carinii

| HISTOLOGIC FINDINGS (methenamine silver) | DIRECT FLUORESCENT ANTIBODY TEST | | |
|---|---|---|---|
| | POSITIVE | NEGATIVE | TOTAL |
| Positive | 9 | 0 | 9 |
| Negative | 2 | 4 | 6 |
| Total | 11 | 4 | 15 |
| Agreement | 9/11=82% | | 4/4=100% |

Results of Indirect Fluorescent Antibody (IFA) tests are recorded in Table 6 for 15 DFA-positive patients. Two-fold or greater rises in serum antibody titers were observed in 5 paired sera by the IFA test. The titer of a single serum from each of 10 suspects in whom P. carinii were identified by DFA varied from 1:4 to 1:128 when titrated against rat P. carinii, using labeled rabbit anti-human IgG. Single serum samples from 3 patients taken after 4 weeks of pentamidine treatment exhibited high IFA titers. The acute sera usually showed lower titers, whereas the titers of sera taken 2 to 4 weeks after pentamidine therapy reached high levels (1:64 to 1:256). Two patients who were known to have congenital agammaglobulinemia did not show antibody reaction beyond a 1:4 dilution of sera. In addition to the data in Table 6, the IFA titers of 4 individuals whose sputa were negative by DFA were found to be relatively low, ranging from 1:8 to 1:32.

TABLE 6.

Indirect Fluorescent Antibody Titers of Patients
Positive by Direct Fluorescent Antibody Test

| | | | | | INDIRECT FA TITERS | | |
|---|---|---|---|---|---|---|---|
| NO. | PATIENTS | AGE* | UNDERLYING DISEASES | HISTOLOGY | Acute Sera | Convalescent sera | Mother's Sera |
| 1. | S.H. | 7y | Congenital Agammaglob. | Positive | 1:4 | ND*** | 1:64 |
| 2. | K.B. | 2y | Congenital Agammaglob. | | 1:4 | ND | 1:32 |
| 3. | N.R. | 7y | Leukemia | | 1:8 | ND | |
| 4. | B.Z. | 3y | Leukemia | Positive | 1:8 | ND | |
| 5. | M.B. | 6y | Leukemia | | 1:16 | 1:128 | |
| 6. | D.K. | 56y | Systemic Lupus Erythematosus | | 1:16 | 1:128 | |
| 7. | W.C. | 5y | Leukemia | | 1:32 | 1:256 | |
| 8. | F.M. | 8y | Leukemia | | 1:16 | 1:128 | |
| 9. | V.J. | 3w | Respiratory distress | | ND | 1:16 | |
| 10. | C.R. | 62y | Sarcoma | | ND | 1:128 | |
| 11. | Z.R. | 32y | Hodgkin's disease | | ND | 1:16 | |
| 12. | P.C. | 9y | Leukemia | | 1:8 | 1:128 | |
| 13. | T.C. | 2y | Leukemia | | ND | 1:128 | |
| 14. | R.H. | 13y | Hodgkin's disease | Positive | ND | 1:64 | |
| 15. | P.J. | 9d | Respiratory distress | | 1:16** | ND | 1:128** |

*y=year,
w=week,
d=day
***ND=not tested
**IgG and IgM titers

In Table 7 the IFA results are correlated with the DFA findings on specimens from the same patients, with the exception of the 2 with congenital agammaglobulinemia (Table 7). Of the convalescent sera which were positive by DFA, 61.5% showed high antibody titer.

TABLE 7

Correlation between Direct and
Indirect Fluorescent Antibody Test

| Indirect Fluorescent Antibody Test | Direct Fluorescent Antibody Test | | |
|---|---|---|---|
| | Positive | Negative | Total |
| Rise in Titer | 8 | 0 | 8 |
| No rise in Titer | 5 | 4 | 9 |
| Total | 13 | 4 | 17 |
| Agreement | 8/13=61.5% | | 4/4=100% |

Because Gomori's methenamine silver (GMS) staining of pulmonary tissue has been recommended for the diagnosis of PP, this staining method was applied to sputa and tracheal aspirates. In order to compare the sensitivity of the DFA with this conventional staining method, duplicate smears of tracheal aspirates from 6 patients confirmed by GMS staining were tested by each of the 2 staining methods. Conclusive identification of *P. carinii* was not possible in the material from any of the 6 patients because of the difficulty is discriminating between this organism and yeast cells. By the DFA method, the same material from all 6 patients was definitely positive.

*Pneumocystis carinii* pneumonitis in this country is almost always related to some form of immunologic deficiency which, in turn, engenders the activation of latent infection or increases the susceptibility to primary infection. Identification of *P. carinii* in tracheal aspirates has been seldom successful, and diagnosis has depended on plumonary biopsy during the advanced stage of the disease. I have found that the examination of sputa or tracheal aspirates by using the DFA procedure of the present invention is reliable and can be substituted for biopsy in many instances.

In the group of 68 patients with diffuse interstitial pneumonitis, 33 or 47.2% were DFA-positive. It is of interest that this percentage agrees well with the results by B. Goodell et al. "*Pneumocystis carinii*: The spectrum of diffuse interstitial pneumonia in patients with neoplastic disease." Ann Intern. Med. 72:337-340 (1970) that 44% of their cases of diffuse interstitial pneumonitis were identifiable as PP by histological examination.

In the control group, *P. carinii* were identified in 3 patients (6%). While E. Stopka, et al "Morphologische und Kulturelle Untersuchungen an Pneumocysten in Sputum und Lungen material. Z. Kinderheilkd."79:2-46–263 (1957) gave no precise figures, they stated that *P. carinii* were observed in sputa from control infants but that the frequency was significatly lower than in the test group. In contrast to this, G. Robillard et al "Plasma cell pneumonia in infants. Review of 51 cases." J. Canad. Ass. Radiol. 16:161–167 (1965) could not detect the organism in infants without symptoms but with histories of contact with known cases. The occasional finding of *P. carinii* in clinically negative persons probably represents inapparent infection, as described by W. Sheldon, "Plumonary *Pneumocystis carinii* infection." J. Pediat. 61-780–791 (1962) and J. Esterly, "*Pneumocystis carinii* in lungs of adults at autopsy." Amer Rev. Resp Dis. 97:935–937 (1968).

In patients with advanced PP, repeated sputum examinations were not necessary; the parasites were detected in the first specimen from each of 9 patients with histologically confirmed diagnoses. However, in the early stages of PP, or for detection of possible carriers, concentrated material should be examined because the number of organisms may be expected to be fewer than in specimens from advanced cases. Likewise, for very viscous specimens or when a large amount of sputum must be examined, treatment with a mucolytic agent and concentration of the specimen are indicated.

Inhibition of FA staining by surface-coating antibodies on the *P. carinii* was not a problem in general, even without pretreatment of the specimens. However, in one instance a partial blocking phenomenon was observed in sputum samples from a patient who had a combined immune deficiency disease with a history of recurrent respiratory involvement of unkown cause. The raw specimen stained by the DFA procedure revealed markedly reduced intensity of staining of *P. carinii* compared with the brilliant staining reaction of the treated specimens. Therefore, at times, one may expect to find a blocking phenomenon in the DFA procedure with untreated specimens. This factor may be related to the duration of the infection or the immune state of the patient or both. It may be of significance that *P. carinii* were not revealed in a biopsy specimen from this patient. However, he may have been a chronic carrier of *P. carinii*. Except for this case, however, inhibition of DFA staining was not encountered, perhaps because almost all of the specimens tested were from patients who were receiving intensive immunosuppressive chemotherapy or had primary immunological deficiency disorders and therefore did not possess enough anti-bodies to bind antigens of *P. carinii* in vivo.

As pointed out by D. Rifkind, et al, "*Pneumocystis carinii* pneumonia: Studies on the diagnosis and treatment." Ann. Intern. Med. 65:943–956 (1966) there is no satisfactory serologic method for antibody assay for PP patients in a state of secondary immunologic incompetence. It is believed that these patients are unable to synthesize antibodies because of impaired cellular function during administration of the suppressants. Recently C. Norman et al, "A preliminary report of an indirect fluorescent antibody test for detecting antibodies to cysts of *Pneumocystis carinii* in human sera." Amer. J. Clin. Path. 58:170–176 (1972) reported a total of 46% of IFA positive sera from 89 individuals who had confirmed or suspected PP as a complication of immunosuppressive therapy. On the other hand they stated that negative IFA reactions were obtained in sera during the acute phase of fatal infections.

In the present study, the sera of 8 or 15 patients in whom *P. carinii* was identified by DFA showed IFA titers of 1:64 or greater; the 4 paired sera showed more than a 4-fold rise. The acute phase sera usually showed lower titers, whereas sera taken 2 to b 4 weeks after therapy showed moderate to high titers (Table 6). For the purpose of analysis, an IFA titer of 1:64 or higher was considered presumptive evidence of current or previous infection. On the other hand, 4 of the 35 clinically positive patients in whom *P. carinii* were not detected by DFA showed IFA titers of 1:8 to 1.32. Although detailed information on the kinds of immunosuppressants used and their doses and duration of administration is not available in all cases studied, these factors may have affected the serum antibody titers. Nevertheless, the IFA results on the paired sera demonstrated rises in titers which are considered to indicate an immune response.

Cross-reaction with other organisms, especially yeast species in the upper respiratory tract, did not create difficulty in identifying *P. carinii*. Freshly isolated yeast cells, primarily species of Candida, exhibit varying degrees of bluish non-specific fluorescence around the cell walls, but after counterstaining the cells usually appear orange-red. The yeast cells as well as the *P. carinii* stand out clearly in distinguishing one from the other. The non-specific staining reaction of C. albicans cells is distinctive and, furthermore, the fungus, unlike *P, carinii*, may exhibit budding or pseudophyphae in the smear preparations. In case of doubt, the appropriate labeled anti-fungal reagent should be used as a control. The chances of contamination by yeast cells is greater with sputa than with carefully aspirated tracheal material. Therefore, tracheal or trans-tracheal aspirates are the specimens of choice.

*P. carinni* pneumonitis may be complicated by a concomitant infection with other opportunistic pathogens L. Rosen, et al "*Pneumocystis carinii* pneumonia: A clinicopathologic study of 20 patients with neoplastic diseases". Amer. J. Med. 53:428—436 (1972) and A. Theologides, et al "Concomitant opportunistic infection with toxoplasma, pneumocystis and cytomegalovirus." Minnesota Medicine. 53:615—619 (1970) DFA tests for *P. carinii* in tracheal aspirates should be included along with examination for complicating pathogens.

The importance of early diagnosis is well recognized Bradshow, et al, "*Pneumocystis carinii* pneumonitis: Diagnosis and treatment". Ann Intern Med. 73:775–777 (1970) and M. Luna, et al, "*Pneumocystis carinii* pneumonitis in cancer patients." Texas Reports Biol. and Med. 30:41–56(1972). As shown in Table 4, of 33 patients with respiratory disease only suggestive of PP, 8 were DFA-positive. Although detailed follow-up was not available, these positive findings probably indicate early or inapparent infection.

Failure of prior art staining procedures to identify *P. carinii* in the sputa or tracheal aspirates of PP patients has been reported by several workers. Rifkind et al, cited above diagnosed only one of their 4 patients before death; J. Ruskin, et al, "The compromised host and infection. I. *Pneumocystis carinii* pneumonia." JAMA. 202:1070-1074 (1967); J. Robbins, et al "Successful treatment of *Pneumocystis carinii* pneumonitis in patients with congenital hypogammaglobulinemia." New Eng. J. Med. 272:708–713 (1965), Jacobs et al., and Rosen et al. reported unsuccessful results, even after careful searching of their stained preparations.

In a small series of histologically positive patients *P. carinii* could not be identified with certainty by the Gomori's methenamine silver techinque applied to sputa, tracheal aspirates or trans-tracheal aspirates, whereas in each case *P. carinii* were found by the DFA method.

This data indicates that, at least for some patients, the DFA method is superior to the widely accepted methenamine silver staining procedure for examination of sputa or tracheal aspirates and that the DFA procedure can give reliable laboratory assistance in the diagnosis of PP and in the recognition of inapparent infection with *P. carinii*. Also it fills the critical need for an easily performed laboratory test which is suitable for frequent repetition during the prolonged period of treatment. In addition, it offers promise as a research procedure. For example, it could furnish a criterion for judging the value of therapeutic measures.

In the preferred embodiments of the invention described above, the following compositions which were used contained the following ingredients.

THE EAGLE MINIMUM ESSENTIAL MEDIUM (MEM) contained:

| Composition: | Material | Amount Mg/liter |
|---|---|---|
| Amino acids | mM | |
| L-arginine | 0.6 | 105 |
| L-histidine | 0.2 | 31 |
| L-isoleucine | 0.4 | 52 |
| L-leucine | 0.4 | 52 |
| L-lysine | 0.4 | 58 |
| L-phenylalanine | 0.2 | 32 |
| L-threonine | 0.4 | 48 |
| L-tryptophane | 0.05 | 10 |
| L-valine | 0.4 | 46 |
| L-cystine | 0.1 | 24 |
| L-methionine | 0.1 | 15 |
| L-tyrosine | 0.2 | 36 |
| L-glutamine | 2.0 | 292 |
| Vitamins | | |
| Thiamine | | 1 |
| Riboflavin | | 0.1 |
| Pantothenate | | 1 |
| Pyridoxal | | 1 |
| Nicotinamide | | 1 |
| Choline | | 1 |
| i-inositol | | 2 |
| Folic acid | | 1 |
| Carbohydrate | | |
| Glucose | 5.5 | 1000 |
| Salts | | |
| NaCl | 116 | 6800 |
| KCl | 5.4 | 400 |
| $CaCl_2$ | 1.8 | 200 |
| $MgCl_2.6H_2O$ | 1.0 | 200 |
| $NaH_2PO_4.2H_2O$ | 1.1 | 150 |
| $NaHCO_3$ | 23.8 | 2000 |

| EARLE BALANCED SALT SOLUTION | | HANK'S BALANCED SALT SOLUTION |
|---|---|---|
| Material | Amount | Amount |
| NaCl | 6.8 gm/liter of water | 8.0 gm/liter of water |
| KCl | 0.40 | 0.4 |
| $MgSO_4$ | 0.10 | 0.20 |
| $NaH_2PO_4$ | 0.125 | 0.152 |
| $NaHCO_3$ | 2.20 | — |
| Glucose | 1.00 | 1.0 |
| $CaCl_2$ | 0.20 | 0.14 |
| $KH_2PO_4$ | — | 0.060 |

BUFFERS

1. Phosphate-buffered saline, pH 7.6 (PBS)

| | |
|---|---|
| $Na_2HPO_4$ (anhydrous;MW, 141.96) | 1.20 gm |
| $NaH_2PO_4.H_2O$ (MW, 137.99) | 0.22 |
| NaCl (MW, 58.44) | 8.50 |
| Distilled water to make | 1000.0 ml |

2. Phosphate buffer, pH 6.3, 0.0175M (for DEAE chromatography) (PB)

| | |
|---|---|
| $Na_2HPO_4$ in 1 liter of distilled water | 1 part |
| $NaH_2PO_4$ in 1 liter of distilled water | 2 parts |

3. Saline solutions (for DEAE chromatography)
   2M stock solution:
   NaCl 11.69 gm
   PB 100 ml (phosphate buffer from (2) above
   0.125M NaCl:
   6.25 ml of 2M NaCl
   93.75 ml of phosphate buffer, pH 6.3

4. Carbonate buffer, pH 9.5, 0.5M

| | |
|---|---|
| a. $Na_2CO_3$ (anhydrous, MW. 105.99) | 5.3 gm |
| 0.85% saline | 100 ml |
| b. $NaHCO_3$ (anhydrous, MW, 84.01) | 4.2 gm |
| 0.85% saline | 100 ml |
| c. Add 5.8 ml of (a) to 10.0 ml of (b) and adjust to pH 9.5 | |

What is claimed is:

1. The process of producing pneumocystis carinii antiserum conjugated with fluorescein isothiocyanate comprising a. digesting out tissue proteins from a homogenized and clarified *pneumocystis carinii* organism suspension containing tissue obtained from an infected host, purifying the obtained suspension by density gradient centrifugation to secure *pneumocystis carinii* organisms which are substantially free of other antigens;

b. immunizing a host with the purified *pneumocystis carinii* organism containing suspension and isolating the antiserum globulin fraction containing the specific antibody for *pneumocystis carinii* antigens from the hyperimmune serum produced; and c. conjugating said antiserum globulin with a fluorescent dye.

2. The process of claim 1, in which said fluorescent dye is fluorescein isothiocyanate.

3. The process of claim 1, in which there is employed in said digesting step a protolytic enzyme selected from the group consisting of trypsin, chymotrypsin, pepsin, collagenase, and pronase.

4. The process of claim 1, in which there is employed in said digesting step a said protolytic enzyme which is trypsin.

5. The process of claim 1, in which said digested *pneumocystis carinii* containing material is purified using a sucrose gradient.

6. The process of claim 1, in which said *pneumocystis carinii* tissue is lung tissue obtained from rats and humans.

7. The process of claim 1, in which said immunized host is selected from the group consisting of rabbits, horses goats and monkeys.

8. The process of claim 1, in which said immunized host is a rabbit.

9. The process of claim 1, in which said process of producing said purified *P. carinii* suspension comprises homogenizing the infected lung tissue in Eagle minimal essential medium with Hank solution containing penicillin and streptomycin, clarifying the solution obtained and discarding the sediment, digesting this mixture with trypsin, separating and discarding the sediment, centrifuging the supernatant fluid and reconstituting the sediment to make a 10–20% suspension of the antigen organisms, fractionating the suspension by sucrose density centrifugation and collecting the fractions.

10. The process of claim 9, in which said process of producing said antiserum comprises immunizing rabbits with the purified *P. carinii* suspension, then separating the *P. carinii* antibodies from other antibodies by absorption of the other antibodies with mouse tissue powder.

11. The process of claim 10 in which said process of conjugating said antiserum globulin with fluorescein isothiocyanate comprises combining an equal volume of antiserum and saturated ammonium sulfate solution having a pH of 7 and incubating the mixture at 4° C, centrifuging the mixture and collecting the precipitate, dialyzing the globulin containing fraction in a saline solution to eliminate ammonium ions, reacting the globulin with the fluorescein isothiocyanate, removing the unbound dyes and fractionating the conjugate in a diethylamino-ethyl-cellulose anion exchange column to obtain the fraction of optimum F/P ratio of antibodies.

12. The process of claim 11, in which said F/P ratio is 1 to 3.

13. The process of claim 1, in which the dye to protein ratio is 1 to 3.

14. The process of detecting *pneumocystis carinii* organisms comprising staining said organisms in sputum, trachael aspirate or materials which may be infected with said organisms with *pneumocystis carinii* antiserum conjugated with fluorescent dye and observing fluorescence when the organisms are present.

15. *Pneumocystis carinii* antiserum globulin conjugated with fluorescein isothiocyanate.

16. The fluorescent dye conjugated *pneumocystis carinii* antiserum globulin produced by the process of claim 1.

17. The process of producing a *Pneumocystis carinii* antigen which comprises digesting out serum and tissue proteins from a homogenized and clarified *Pneumocystis carinii* organism suspension containing tissue obtained from an infected host, purifying the obtained suspension by density gradient centrifugation, to obtain *Pneumocystis carinii* organisms substantially free of other antigens.

18. The process of producing an antiserum globulin fraction containing the specific antibody for *Pneumocystis carinii* which comprises:

a. digesting out serum proteins from homogenized and clarified *Pneumocystis carinii* organism suspension containing tissue obtained from an infected host, purifying the obtained suspension by density gradient centrifugation to obtain *Pneunocystic carinii* organisms which are substantially free of other antigens;

b. immunizing a host with the purified *Pneumocystis carinii* organism containing suspension and isolating the antiserum globulin fraction containing the specific antibody for *Pneumocystis carinii* antigens from the hyperimmune serum produced.

19. The process of detecting *Pneumocystis carinii* organisms which comprises making smears of the purified organism or trypsinized impression smears of infected tissue, fixing the smears with acetone, and staining the fixed smears with the labeled antiserum prepared by the method of claim 1.

20. The process of claim 19 which further comprises counterstaining the smear.

* * * * *